United States Patent [19]

Raynor

[11] Patent Number: 4,751,073

[45] Date of Patent: Jun. 14, 1988

[54] SELECTED 2,2,6,6-TETRAALKYL-4-PIPERIDINYL DERIVATIVES AND THEIR USE AS LIGHT STABILIZERS

[75] Inventor: Robert J. Raynor, North Branford, Conn.

[73] Assignee: Olin Corporation, Cheshire, Conn.

[21] Appl. No.: 57,845

[22] Filed: Jun. 3, 1987

[51] Int. Cl.$^4$ .............. A61K 7/42; C07D 211/30; C07D 211/32; C07D 211/08

[52] U.S. Cl. ............................. 424/59; 546/190; 546/191; 524/102; 252/401; 252/405

[58] Field of Search .................. 546/190, 191; 424/59

[56] References Cited

U.S. PATENT DOCUMENTS

| | | | |
|---|---|---|---|
| 3,374,246 | 3/1968 | Marcus et al. | 260/345.9 |
| 3,936,418 | 2/1976 | Pond et al. | 260/308 |
| 4,086,204 | 4/1978 | Cassandrini et al. | 260/45 P |
| 4,104,248 | 8/1978 | Cantatore | 260/45.8 N |
| 4,127,586 | 11/1978 | Rody et al. | 260/308 |
| 4,166,814 | 9/1979 | Karrer | 546/190 |
| 4,191,683 | 3/1980 | Brunetti et al. | 546/190 |
| 4,233,410 | 11/1980 | Rody et al. | 525/123 |
| 4,233,412 | 11/1980 | Rody et al. | 525/167 |
| 4,250,268 | 2/1981 | Rody et al. | 525/100 |
| 4,356,287 | 10/1982 | Loffelman et al. | 525/204 |
| 4,548,973 | 10/1985 | Raynor | 524/102 |

FOREIGN PATENT DOCUMENTS

| | | | |
|---|---|---|---|
| 0172413 | 2/1986 | European Pat. Off. | 546/190 |
| 2143537 | 2/1985 | United Kingdom | 546/190 |
| 2143538 | 2/1985 | United Kingdom | 546/190 |
| 0671245 | 6/1985 | U.S.S.R. | 546/190 |

*Primary Examiner*—Mary C. Lee
*Assistant Examiner*—J. Richter
*Attorney, Agent, or Firm*—Dale Lynn Carlson

[57] ABSTRACT

2,2,6,6-tetraalkyl-4-piperidinyl derivatives and, more specifically, the N,N'-bis(2,2,6,6-tetraalkyl-4-piperidene)2,2'-diamino-2,2'-dihydrocarbyl divinyl ketones wherein the alkyl groups have independently from one to about eight carbon atoms and said hydrocarbyl moieties are selected from the group consisting of alkyls having between one and about eight carbon atoms, aryl, alkaryl, and aralkyl groups having between one and about twenty carbon atoms.

These compounds are useful as UV light stabilizers in plastics and cosmetics (e.g. sunscreens).

7 Claims, No Drawings

SELECTED 2,2,6,6-TETRAALKYL-4-PIPERIDINYL DERIVATIVES AND THEIR USE AS LIGHT STABILIZERS

FIELD OF THE INVENTION

This invention relates to selected 2,2,6,6-tetraalkyl-4-piperidinyl derivatives as novel compositions of matter and their use as ultraviolet light stabilizers.

BACKGROUND OF THE INVENTION

Ultraviolet (UV) radiation having wavelengths from about 280 to about 400 nm may cause the degradation of exposed organic matter such as plastics and will burn and/or induce tumors in human skin. To negate these undesirable actions, plastics and the like are protected by chemical additives called UV stabilizers and human skin and hair are protected by cosmetics containing UV stabilizers or sunscreens.

To be viable for commercial applications, a UV stabilizer should inhibit or dramatically retard degradation of organic material exposed to light by one or a combination of mechanisms such as the absorption of light energy or the entrapment of the destructive free radicals produced in the material by its interaction with light or oxygen or both. Absorbers should preferably have a strong ultraviolet light absorptivity at wave lengths between 280 and 400 nm. A light stabilizer should also be photostable by itself, be compatible with the substrate (e.g. plastic or cosmetic emulsion) in which it is used as an additive, be non-volatile at the high temperatures involved during incorporation and processing stages as well as during certain end uses, possess low color, be chemically inert, have low or no toxicity or skin sensitization/irritation properties, be non-mutagenic, and be stable to the environments experienced during its processing and application. Furthermore, for human sunscreen use, it is also desirable that the UV stabilizer be relatively insoluble in water.

Accordingly, it is an object of the present invention to provide a novel class of UV light stabilizer compounds.

A specific object of this invention is to provide a novel class of UV light stabilizer compounds which may be used to stabilize ultraviolet degradable organic compositions, particularly plastics such as polyethylene and polypropylene, against deterioration resulting from the exposure to such UV radiation.

Another specific object is to provide a novel class of UV light stabilizer compounds which might be used in human cosmetic products such as sunscreens, hair dyes and hair tinting compositions to prevent or retard UV radiation from penetrating the human skin or hair.

These and other objects and features of the invention will be made apparent from the following more particular description of the invention.

SUMMARY OF THE INVENTION

The present invention, therefore, is directed to 2,2,6,6-tetraalkyl-4-piperidinyl derivatives and, more specifically, the N,N'-bis(2,2,6,6-tetraalkyl-4-piperidinyl)2,2'-diamino-2,2'-dihydrocarbyl divinyl ketones wherein the alkyl groups have independently between one and about eight carbon atoms and the hydrocarbyl moieties are selected from the group consisting of alkyls having between one and about eight carbon atoms, aryl, alkaryl, and aralkyl groups having between one and about twenty carbon atoms, and substituted derivatives thereof.

Also, the present invention is directed to organic compositions susceptible to ultraviolet degradation being stabilized against such degradation by incorporating therein effective stabilizing amount of said 2,2,6,6-tetraalkyl-4-piperidinyl derivatives.

Still further, the present invention is directed to a process for stabilizing an organic composition, such as a plastic, a coating or the like, susceptible to ultraviolet degradation comprising incorporating into said organic composition an effective stabilizing amount of said 2,2,6,6-tetraalkyl-4-piperidinyl derivatives.

Furthermore, the present invention is directed to human sunscreen compositions which effectively prevent or retard UV light from penetrating human skin or hair, said sunscreen compositions comprising an effective screening amount of said 2,2,6,6-tetraalkyl-4-piperidinyl derivatives.

And even further, the present invention is directed to a process for substantially screening out UV light from human skin or hair comprising applying a sunscreen composition on said skin or hair to prevent or retard UV light from penetrating to said skin or hair, said sunscreen composition comprising an effective screening amount of said 2,2,6,6-tetraalkyl-4-piperidinyl derivatives.

DETAILED DESCRIPTION OF THE INVENTION

The derivatives of 2,2,6,6-tetraalkyl piperidine of the present invention may be made by reacting the appropriate pyrone, such as 2,6-dimethyl-γ-pyrone or 2,6-diethyl-γ-pyrone, with a substituted piperidine such as 4-amino-2,2,6,6-tetraalkyl (preferably tetramethyl) piperidine, preferably in an aqueous solvent at a reaction temperature from about 40° to about 200° C. This reaction is illustrated by the formation of N,N'-bis(2,2,6,6-tetramethyl-4-piperidinyl)2,2'-diamino-2,2'-dimethyl divinyl ketone by the reaction of 1 mole of 2,6-dimethyl-γ-pyrone with 2 moles of 4-amino-2,2,6,6-tetramethylpiperidine as shown in the following Equation A:

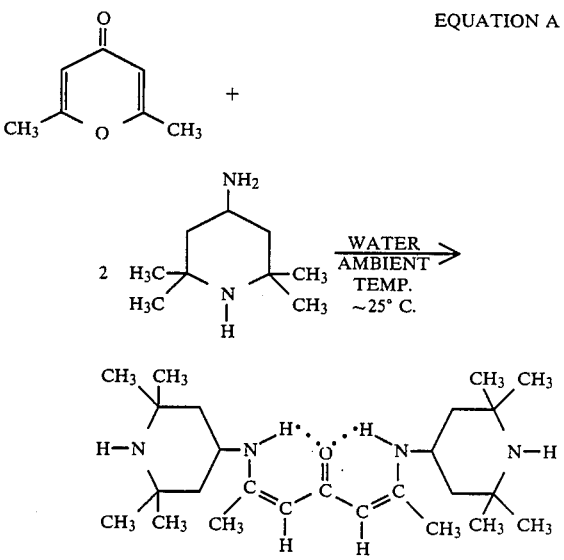

EQUATION A

Another name for this Equation A product is 2,6-bis(2,2,6,6-tetramethylpiperidinyl-4-amino)-2,5-heptadien-4-one.

The hydrogen on the nitrogen atom of the tetramethylpiperidine portion of the compound made by the reaction of Equation A, above, may be replaced with a lower alkyl group. Direct replacement thereof can be effected by treatment of the piperidine with a reactive alkyl halide (such as an alkyl bromide) in the presence of a strong base (such as sodium bicarbonate) or by reaction with an alkyl tosylate. Also, rather than using 4-amino-2,2,6,6-tetra-methylpiperidine, a corresponding N-alkyl-substituted 2,2,6,6-tetrahydrocarbyl piperidine may be used in its place.

In an alternate embodiment, any 1,3,5-triketone such as, for example, diacetyl acetone could be utilized to form vinyl ketone analogs of 2,6-bis(2,2,6,6-tetramethylpiperidinyl-4-amino)-2,5-heptadien-4-one after rearrangement of the keto to the enol isomer as follows:

EQUATION B

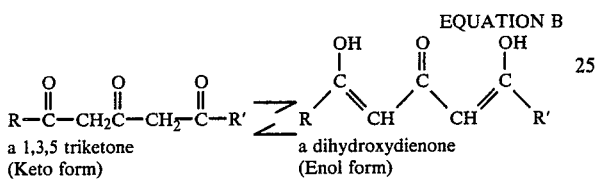

a 1,3,5 triketone (Keto form)    a dihydroxydienone (Enol form)

The dihydroxydienones react in an analogous fashion to the diacetylacetone with 4-amino-2,2,6,6-tetramethyl piperidine to form the vinyl ketone having the following generic formula:

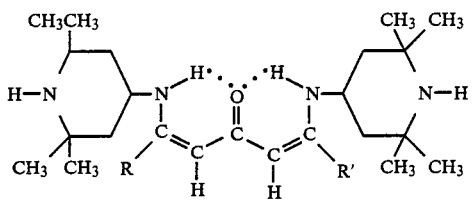

wherein R and R' are independently selected from the group consisting of alkyl, aryl, substituted alkyl, substituted aryl, aralkyl, and alkaryl.

It is also possible to obtain these compounds from other 2,6-pyrones, such as, for example,

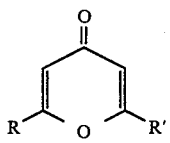

wherein R and R' are defined above.

Also diacetylacetone can be converted to dimethyldiacetyl acetone which then reacts with 4-amino-2,2,6,6-tetramethylpiperidine to give a tetramethyl substituted 2,2,6,6-tetramethyl-4-piperdinyl derivative.

EQUATION C

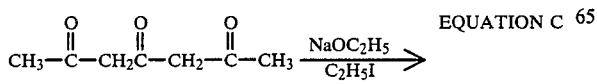

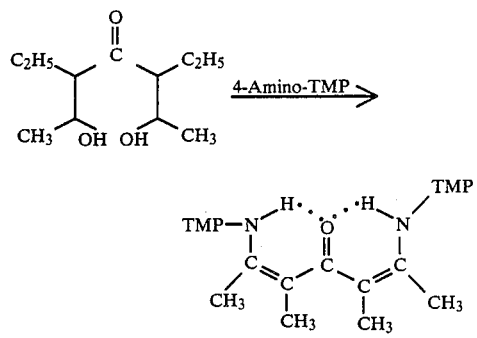

wherein "TMP" denotes

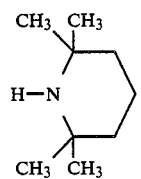

A generic representation of the product of Equation C above is as follows:

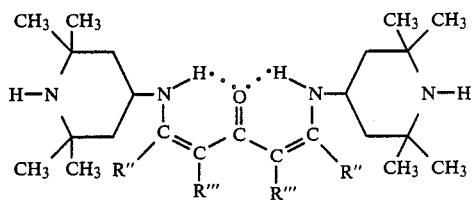

wherein R" is independently selected from the group consisting of alkyl, aryl, substituted alkyl, substituted aryl, aralkyl, and alkaryl, and wherein R''' is independently selected from the group consisting of hydrogen, alkyl, aryl, substituted alkyl, substituted aryl, aralkyl, and alkaryl.

Illustrative examples of R" and R''' are cyanomethyl, methyl, ethyl, propyl, butyl, hexyl, octyl, decyl, dodecyl, allyl, methallyl, but-2-enyl, undec-10-enyl, propargyl, benzyl, methylbenzyl, t-butylbenzyl, hydroxybenzyl, acetyl, propionyl, butyryl, caproyl, benzoyl, 2,3-epoxypropyl, 2-hydroxyethyl and 2-hydroxypropyl.

Note, U.S. Pat. No. 3,374,246, issued Mar. 19, 1968 to E. Marcus et al and assigned to Union Carbide Corporation discloses:

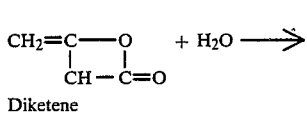
Diketene

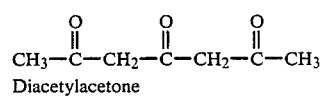
Diacetylacetone

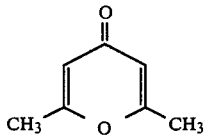

2,6-Dimethylpyrone

The pyrones useful as reactants in making the compounds of the instant invention are suitably produced by the method disclosed in U.S. Pat. No. 3,374,246, incorporated herein by reference.

The reaction used to produce the compounds of the present invention is carried out with a 1:2 mole ratio of the 2,6-dimethyl-γ-pyrone to the piperidine precursor in the presence of a suitable inert solvent, preferably a water solvent. Other useful solvents include polar organic solvents such as dimethylformamide (DMF), $CH_3CN_2$, and the like. However, the use of a water solvent will generally be satisfactory and an organic solvent is generally not necessary, although it can be used as desired.

The reaction temperature and time will both depend upon many factors including the specific reactants used. In most situations, reaction temperatures may advantageously be from about 40° to about 200° C. and reaction times from about 15 minutes or less to about 300 minutes or more may be utilized. The product may be further purified by conventional means such as recrystallization in an inert solvent, franctional distillation, or the like.

The compounds of the present invention are believed to possess a combination of properties which make them advantageous as UV stabilizers. These desirable properties include their non-volatility, their stability under normal storage conditions, and their exceptionally strong maximum absorptivity of UV light in a wavelength range of between about 280 and about 320 nm.

Also in accordance with the present invention, the compounds of the present invention may be utilized as effective ultraviolet stabilizers for UV-degradable organic material or in human sunscreen compositions. In practicing the use as a UV stabilizer for such organic materials, an effective stabilizing amount of one or more of these stabilizers is incorporated into the organic composition susceptible to UV degradation. In practicing the use as a UV stabilizer in human sunscreen composition, an effective screening amount of one or more compounds of the present invention is incorporated into the sunscreen composition which is applied to human skin or hair. It is to be understood that the terms "effective stabilizing amount" and "effective screening amount" as used in the specification and claims herein is intended to include any amount that will prevent or retard UV radiation from either degrading the organic material incorporated therein or penetrating the human skin or hair, respectively. Of course, these amounts may be constantly changing because of possible variations in external parameters such as the intensity of UV radiation based upon changing sunlight conditions.

Generally, amounts of from about 0.01% to about 10% by weight of stabilizer are employed based on the weight, of the organic or carrier material to which the UV stabilizer is added. While a detectable amount of stabilization or screening may be obtained with amounts less than 0.01%, this amount of stabilization or screening would be of little practical utility in a commercial application. Moreover, while amounts greater than 10% by weight provide effective ultraviolet stability and screening, such concentrations are undesirable because of cost and the deleterious effect which such concentrations may have on the mechanical properties of the organic composition in which the UV stabilizer is incorporated. Preferably, the stabilizer is used in an amount of from about 0.1% to about 3% by weight.

Possible organic materials which are susceptible to UV degradation and which may have the compounds of the present invention incorporated therein as UV stabilizers include organic polymers (both thermoplastic and thermosetting polymers). Wholly synthetic polymers such as addition polymers, condensation polymers and condensation polymers crosslinked by addition polymerization may be stabilized with these UV stabilizers. Natural polymers such as polysaccharides, rubber and proteins may also be aided. Also, chemically modified polymers may be employed as substrates as well as other substances such as natural and synthetic light-sensitive waxes, fats and oils, emulsions which contain light-sensitive fatty substances or the above-mentioned polymers.

Exemplary lists of these polymers and other substances are shown in U.S. Pat. No. 4,127,586, which issued to Rody et al on Nov. 28, 1978, and U.S. Pat. No. 3,936,418, which issued to Pond et al on Feb. 3, 1976. Both of these U.S. patents are incorporated herein by reference in their entireties.

Any suitable carrier material which is presently used for human sunscreen compositions may have the compounds of the present invention incorporated therein. Examples of this carrier material for sunscreens include emollients or emulsions of conventional cosmetic chemicals known in the art.

Such organic compositions and sunscreen compositions may contain further additives, pigments, colorants, antioxidants, other UV stabilizers and sunscreens, metal deactivators, phosphites, lubricants, fillers and the like. Pigments and colorants are frequently preferred for use in conjunction with compounds of the present invention since some of these compounds can initially take on a slight yellowish hue which later tends to disappear upon exposure to UV light.

The compounds of the present invention may be incorporated into these organic compositions or sunscreen compositions by any conventional blending technique such as melt-blending, mixing or the like. Alternatively, they may be added onto the surface of such materials or affixed thereto by means of a gel or the like.

The following examples are intended to illustrate, but in now way limit, the present invention. All parts and percentages employed therein are by weight unless otherwise indicated.

EXAMPLE 1

Preparation of N,N'Bis(2,2,6,6-Tetramethyl-4-Piperidinyl)2,2'-Diamino-2,2'-Dimethyl Divinyl Ketone A mixture of 12.4 g (0.1 moles) 2,6 dimethyl-γ-pyrone, 31.3 g (0.2 moles) 4-amino-2,2,6,6-tetramethyl piperidine and 110 ml water was heated to 70° C. and stirred gently until a homogeneous solution was obtained. The solution was allowed to cool slowly to room temperature and then to stand without stirring for 39 days. During this period, solids were continuously formed and periodically removed by filtration. The first collection of solids which was isolated after 24 hours was combined with those subsequently cooled from the filtrates to give a total of 33.4 g (80 percent). Recrystallization of these solids from heptane gave 23.0 g (55 percent) of very light crystals having a melting point of 168°-170° C. These crystals were confirmed by elemental and NMR analysis to be the title compound (also identivied herein as "EXAMPLE 1 compound").

The ultraviolet light absorptivity properties of this compound were measured by means of a spectrophotometer and the results are as shown below:

TABLE I

| Example | Wave Length λ, Max | Absortivity[1] L/g-cm | Molar[2] Absorptivity |
|---|---|---|---|
| EXAMPLE 1 Compound | 376 | 123.8 | 51,757 |
| Comparison Para-aminobenzoic acid | 290 | 132.8 | 18,200 |

[1]Measured on a Perkin-Elmer spectrophotometer, Model No. 330. Absorptivity (a) equals $\frac{A}{bc}$ where A = absorbance (also called optical density) and is an observed (experimentally determined) value; b = cell size; and c = concentration of compound in solvent.
[2]Molar absorptivity = absorptivity (a) times molecular weight.

This data indicates the compound of EXAMPLE 1 is a very good absorber of ultraviolet light energy, as compared to a commercial suntan lotion sunscreen, namely, p-aminobenzoic acid.

The light stabilizing performance of this compound was then compared to that of commercial light stabilizers. This was done by the incorporation of the compound in a plastic substrate and subjecting a sample of the plastic to weathering simulation tests. These tests and the results they produced are as follows:

Test 1—Primary Screening Test—UV Light Stabilizer Effectiveness 1,4-Polybutadiene in the presence of UV light and air is easily photooxidized. The rate and extent of photooxidation can be estimated by determining the range and magnitude of the hydroxyl and carbonyl groups formed in the polymer when it is subjected to strong UV light in the presence of air. The measurement of these key groups is made by infrared spectroscopic techniques.

In this portion of the example, 1,4-polybutadiene was purified by solvent precipitation, and a solution of the pure polymer was doped with a known concentration of a light stabilizing additive. Thin film was then cast from this solution and in turn subjected to a UV light source while in the presence of air. The film was periodically withdrawn from the test apparatus and its hydroxyl and/or carbonyl content measured by IR. A comparison of the rate and magnitude of the hydroxyl and/or carbonyl groups present in the polymer film was then made against a blank and selected controls. For the purposes of comparison, an arbitrary induction period was assigned. This induction period is defined as the time required for the absorbance at 3450 cm$^{-1}$ (hydroxyl) to reach 0.2 absorbance units. The ratio of the measured induction period for the test specimens to the measured induction period for the control provides a convenient means of comparing the performance of the test candidates with each other and the control. This is expressed as $t/t_o$.

Using this test, the following results were obtained:

TABLE II

| Test Results of Primary Screening | |
|---|---|
| Additive | $t/t_o$ |
| none (control) | 1.0 |
| CYASORB UV-531* | 2.1 |
| CYASORB UV-1084** | 3.9 |
| EXAMPLE 1 compound | 5.7 |

*A benzophenone light stabilizer (product of American Cyanamid).
**A nickel chelate light stabilizer (product of American Cyanamid).

The results given in TABLE II indicate that the vinyl ketone compound of EXAMPLE 1 is an effective light stabilizer. This is shown by the data indicating that the time required for the sample containing EXAMPLE 1 to reach the 0.2 absorbance units was 5.7 times that of the control compared to two commercial light stabilizers (CYASORB UV-531 and CYASORB UV-1084) which reached the same level 0.2 absorbance units at times which were only 2.1 and 3.9 times that of the control respectively.

Test 2—Test of Instant Versus Comparison Compounds as Plastic Additive Light Stabilizers Various test sample formulations were prepared by dry blending several UV stabilizers and an antioxidant[1] into unstabilized powdered polypropylene[2] or into LLDPE polyethylene[3]. The final polypropylene formulation contained 0.2% by weight of UV stabilizer, 0.05% antioxidant and the balance powdered polypropylene. The final LLDPE formulation contained 0.10% by weight of UV stabilizer, and the LLDPE manufacturer-supplied amount of IRGANOX 1076 antioxidant. The antioxidant was used to stabilize the polyethylene during the high temperature extrusion. These mixtures were extruded into 25 mil thick polypropylene films or 5 mil thick LLDPE films in a ¾ inch plastic-making extruder at 250° C. These films were then tested in a Q-U-V Accelerated Weather Tester (manufactured by Q-Panel Corporation) in accordance with ASTM G53-77 standard procedures.

[1] IRGANOX 1076 antioxidant made by Ciba-Geigy Corporation.
[2] PRO-FAX 6501 polypropylene made by Hercules Inc.
[3] GRSN-7047, an LLDPE product of Union Carbide Corporation.

As can be seen from the following TABLES III and IV, the ability of the compound of EXAMPLE 1 to protect LLDPE polyethylene against degradation under simulated weathering conditions is comparable to that of well-known, commercially-available light stabilizers.

TABLE III

Comparative Test Results
Q-UV Accelerated Weathering
Polypropylene

| UV Stabilizer | Days to Failure | Yellowness Index[1] Initial | at Failure |
|---|---|---|---|
| Base Resin (PRO-FAX 654) | 7 | 0.6 | 4.6 |
| Resin With IRGANOX 1076 | 8 | 1.2 | 2.5 |
| TINUVIN 770 | 31 | 1.3 | 2.0 |
| CYASORB UV-531 | 7 | 1.8 | 40.3 |
| CYASORB UV-1084 | 10 | 6.9 | 17.4 |
| CYASORB UV-3346 | 22 | 0.9 | 1.7 |
| TINUVIN 622-LD | 24 | 0.6 | 3.3 |
| TINUVIN 944 | 20 | 0.4 | 2.1 |
| EXAMPLE 1 compound | 22 | 1.8 | 1.1 |

[1]Hunter Color, Yellowness Index = $\frac{(1.02x - 0.47z)125}{Y}$

TABLE IV

Comparative Test Results
Q-UV Accelerated Weathering Tester
LLDPE

| UV Stabilizer | Days to Failure | Carbonyl[1] Index |
|---|---|---|
| Base Resin (GRSN-7047) | 15 | 1.0 |
| TINUVIN 770 | 34 | 0.595 |
| TINUVIN 622LD | 41 | 0.272 |
| TINUVIN 944 | 41 | 0.550 |
| CYASORB UV-531 | 20 | 0.890 |
| CYASORB UV531/ 1084 (1:1) | 20 | 1.0 |
| CYASORB 3346 | 34 | 0.595 |
| EXAMPLE 1 compound | 28 | 0.609 |

[1] Abs. changes in absorbance from 1710 cm$^{-1}$ to 1720 cm$^{-1}$.

Test 3—Tensile Strengths and Percent Elongation Comparisons in LLDPE

The vinyl ketone compound prepared above (i.e., EXAMPLE 1 compound) was compounded with Linear Low Density polyethylene resin, extruded at 250° C., pelletized and compression molded at 200° C. under 20 tons of pressure into 40 mil thick sheets. Plaques and tensile bars cut from the sheets were placed in a xenon arc "Weather-o-meter" weather simulator together with a blank and commercial controls. The tensile strength, and percent elongation of the sample were measured initially and periodically thereafter and recorded. It should be noted that diminishment of these properties over time is a quantitative measure of the amount of photodegradation of the polymer over a period of time.

The results given in TABLE V which follows indicated that the vinyl ketone compound of the instant example performs generally comparably to commercial UV light stabilizers as measured by the tensile strength and percent elongation of compression molded LLDPE containing one of these additives after sustained exposure to xenon light.

TABLE V

Weather-o-Meter Evaluation of
40 Mil Compression-Molding LLPDE
Tensile Strength (psi); Elongation Percent

| | Hrs. to 50% Retention of | |
|---|---|---|
| Additive at 0.25% | Tensile Strength | Elongation |
| Control | 680 | 380 |
| TINUVIN 622LD | 3520 | 4800 |
| CHIMASORB 944LD | 5585 | 5585 |
| TINUVIN 770 | 1900 | 2760 |
| CYASORB UV 531 | 1860 | 1880 |
| CYASORB UV 531/1084 (1:1) | 1860 | 1680 |
| EXAMPLE 1 compound | 2680 | 3640 |

The results given in TABLE V indicate that the vinyl ketone compound prepared in EXAMPLE 1 is an effective light stabilizer.

EXAMPLE 2

Alternate Method of Preparing
N,N'-Bis(2,2,6,6-Tetramethyl-4-Piperidinyl)2,2'-Diamino-2,2'-Dimethyl Divinyl Ketone A solution of 7.1 g (0.05 mole) diacetylacetone and 17.2 g (0.11 mole) 4-amino-2,2,6,6-tetramethylpiperidine in 200 ml water was stirred and reacted at 70° C. for 30 minutes and then cooled slowly to room temperature. Upon cooling to room temperature, crystalline solids were precipitated. These solids were removed from solution by filtration, washed with water and dried in a vacuum oven to give 18.0 g (86 percent) of 2,6-bis(2,2,6,6-tetramethylpiperidinyl-4-amino)2,5-heptadien-4-one MP-168.5° C., which is the same compound as was prepared in EXAMPLE 1 above.

Note that this preparation is a much faster synthesis than that of EXAMPLE 1, requiring a reaction time of only about 30 minutes total time, as compared to 39 days for the EXAMPLE 1 method.

EXAMPLE 3

Proposed Preparation of 2,6-Bis(2,2,6,6-Tetramethyl Piperidinyl-4-Amino)-1,5-Diphenyl-1,4-Pentadien-3-one A mixture of 13.3 g (0.05 mole) of 1,5-diphenyl-1,3,5-pentanetrione[1] and 17.2 g (0.11 mole) 4-amino-2,2,6,6-tetramethylpiperidine in 200 ml. water is stirred at 70°-80° C. for 30 minutes and cooled to room temperature. The solids which are deposited are removed by filtration, washed with water and dried in a vacuum oven to give 2,6-bis(2,2,6,6-tetramethyl piperidinyl-4-amino)-1,5-diphenyl-1,4-pentadien-3-one.

[1] Prepared by known procedures, for example, the procedures disclosed in: (a) R. J. Light and C. R. Hauser, J. Org. Chem., 25, 538 (1960). (b) M. L. Miles, T. M. Harris, and C. R. Hauser, J. Org. Chem., 30, 1007, (1965).

The reaction sequence is as follows:

$$C_6H_5-\overset{\overset{O}{\|}}{C}-CH_2-\overset{\overset{O}{\|}}{C}-CH_2-\overset{\overset{O}{\|}}{C}-C_6H_5 +$$

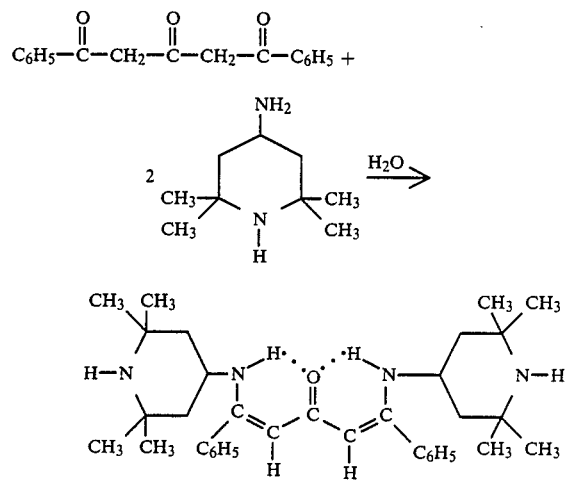

EXAMPLE 4

Proposed Preparation of
N,N'-Bis(2,2,6,6-Tetramethyl-4-Piperidinyl)2,2-Diamino-2,2'-Dimethyl Divinyl Ketone
2,6-Dimethylpyrone A mixture of 23.6 g (0.1 mole) 2,6-diphenyl-γ-pyrone, 31.3 g (0.2 moles) 4-amino-2,2,6,6-tetramethyl piperidine and 110 ml water is heated to 70° C. and stirred gently until a homogeneous solution is obtained. The solution is allowed to cool slowly to room temperature and then to stand without stirring for 39 days. During this period, solids are continuously formed and periodically removed by filtration. The N,N'-bis(2,2,6,6-tetramethyl-4-piperidinyl)-2,2-diamino-2,2'-dimethyl divinyl ketone 2,6-dimethylpyrone is then isolated in accordance with the procedure given in EXAMPLE 1. The product can be confirmed by elemental and NMR analysis to be the title compound.

EXAMPLE 5

Proposed Preparation of Methyl Substituted Analogue of EXAMPLE 1 Compound

A mixture of 17.0 g (0.1 mole) 3,5-dimethyl-2,4,6-heptane trione[1] and 34.4 g (0.22 mole) 4-amino-2,2,6,6-tetramethylpiperidine in 200 ml water is stirred at 70° C. from 30 minutes and then cooled slowly to room temperature. Upon cooling to room temperature, crystalline solids are deposited. These solids are removed by filtration, washed with water and dried in a vacuum oven to give 2,6-bis(2,2,6,6-tetramethylpiperidinyl-4-amino)-1,2,4,5-tetramethyl-1,4-pentadien-3-one.

[1]Prepared from diacetyl acetone by treatment with sodium methoxide and methyl iodide by known procedures.

The reaction sequence is as follows:

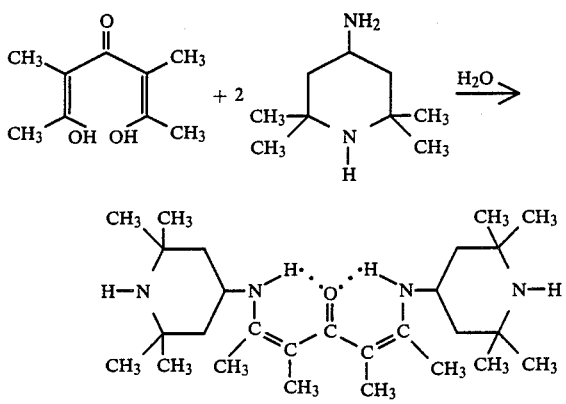

What is claimed is:

1. A 2,2,6,6-tetraalkyl-4-piperidinyl derivative selected from the group consisting of N,N'-bis(2,2,6,6-tetraalkyl-4-piperidinyl)2,2'-diamino-2,2'-dihydrocarbyl divinyl ketones, said alkyl groups independently having from one to about eight carbon atoms and said hydrocarbyl moieties being optionally substituted and selected from the group consisting of cyanomethyl, methyl, ethyl, propyl, butyl, hexyl, octyl, decyl, dodecyl, allyl, methallyl, but-2-enyl, undec-10-enyl, propargyl, phenyl, benzyl, methylbenzyl, t-butylbenzyl, hydroxybenzyl, acetyl, propionyl, butyryl, caproyl, benzoyl, 2,3-epoxypropyl, 2-hydroxyethyl and 2-hydroxypropyl.

2. A 2,2,6,6-tetraalkyl-4-piperidinyl derivative which is N,N'-bis(2,2,6,6-tetramethyl-4-piperidinyl)2,2'-diamino-2,2'-dimethyl divinyl ketone.

3. A sunscreen composition which effectively prevents UV light from penetrating human sklin or hair, said sunscreen composition comprising an effective screening amount of 2,2,6,6-tetraalkyl-4-piperidinyl derivative selected from the group consisting of N,N'-bis(2,2,6,6-tetraalkyl-4-piperidinyl)2,2'-diamino-2,2'-dihydrocarbyl divinyl ketones, said alkyl independently having from one to about eight carbon atoms and said hydrocarbyl moieties being optionally substituted and selected from the group consisting of cyanomethyl, methyl, ethyl, propyl, butyl, hexyl, octyl, decyl, dodecyl, allyl, methallyl, but-2-enyl, undec-10-enyl, propargyl, phenyl, benzyl, methylbenzyl, t-butylbenzyl, hydroxybenzyl, acetyl, propionyl, butyryl, caproyl, benzoyl, 2,3-epoxypropyl, 2-hydroxyethyl and 2-hydroxypropoyl.

4. In a sunscreen composition which effectively prevents UV light from penetrating to human skin or hair, wherein the improvement comprises said composition containing an effective amount of 2,2,6,6-tetraalkyl-4-piperidinyl derivative selected from the group consisting of N,N'-bis(2,2,6,6-tetraalkyl-4-piperidinyl)2,2'-diamino-2,2'-dihydrocarbyl, divinyl ketones, said alkyl independently having from one to about eight carbon atoms and said hydrocarbyl moieties being optionally substituted and selected from the group consisting of cyanomethyl, methyl, ethyl, propyl, butyl, hexyl, octyl, decyl, dodecyl, allyl, methallyl, but-2-enyl, undec-10-enyl, propargyl, phenyl, benzyl, methylbenzyl, t-butylbenzyl, hydroxybenzyl, acetyl, propionyl, butyryl, caproyl, benzoyl, 2,3-epoxypropyl, 2-hydroxyethyl and 2-hydroxypropyl.

5. In a sunscreen composition which effectively prevents UV light from penetrating to human skin or hair, wherein the improvement comprises said composition containing an effective amount of 2,2,6,6-tetraalkyl-4-piperidinyl derivative wherein said derivative is N,N'-bis(2,2,6,6-tetramethyl-4-piperidinyl)2,2'-diamino-2,2'-dimethyl divinyl ketone.

6. In a process for substantially screening out UV light from human skin or hair which comprises applying a sunscreen composition on said skin or hair to prevent or retard UV light from penetrating to said skin or hair; the improvement which comprises said sunscreen composition comprising an effective screening amount of 2,2,6,6-tetraalkyl-4-piperidinyl derivative which is selected from the group consisting of N,N'-bis(2,2,6,6-tetraalkyl-4-piperidinyl)2,2'-diamino-2,2'-dihydrocarbyl divinyl ketones, said alkyl independently having from one to about eight carbon atoms and said hydrocarbyl moieties being optionally substituted and selected from the group consisting of cyanomethyl, methyl, ethyl, propyl, butyl, hexyl, octyl, decyl, dodecyl, allyl, methallyl, but-2-enyl, undec-10-enyl, propargyl, phenyl, benzyl, methylbenzyl, t-butylbenzyl, hydroxybenzyl, acetyl, propionyl, butyryl, caproyl, benzoyl, 2,3-epoxypropyl, 2-hydroxyethyl and 2-hydroxypropyl.

7. In a process for substantially screening out UV light from human skin or hair which comprises applying a sunscreen composition on said skin or hair to prevent or retard UV light from penetrating to said skin or hair; the improvement which comprises said sunscreen composition comprising an effective screening amount of 2,2,6,6-tetraalkyl-4-piperidinyl derivative wherein said derivative is N,N'-bis(2,2,6,6-tetramethyl-4-piperidinyl)2,2'-diamino-2,2'-dimethyl divinyl ketone.

* * * * *